United States Patent
Arthur et al.

(10) Patent No.: US 9,149,317 B2
(45) Date of Patent: Oct. 6, 2015

(54) SURGICAL TOOL HOLDER

(71) Applicant: KYPHON SARL, Neuchatel (CH)

(72) Inventors: Amy L. Arthur, Mountain View, CA (US); Mojan Goshayeshgar, Atherton, CA (US)

(73) Assignee: KYPHON SARL, Neuchatel (CH)

( * ) Notice: Subject to any disclaimer, the term of this patent is extended or adjusted under 35 U.S.C. 154(b) by 132 days.

(21) Appl. No.: 13/790,825

(22) Filed: Mar. 8, 2013

(65) Prior Publication Data
US 2014/0257419 A1  Sep. 11, 2014

(51) Int. Cl.
*A61B 19/00* (2006.01)
*A61B 17/88* (2006.01)
*A61B 17/34* (2006.01)

(52) U.S. Cl.
CPC ........... *A61B 17/88* (2013.01); *A61B 17/3403* (2013.01); *A61B 17/3472* (2013.01); *A61B 2017/3407* (2013.01); *A61B 2017/347* (2013.01)

(58) Field of Classification Search
CPC ..... A61B 19/00; A61B 17/3403; A61B 17/88
USPC ............ 606/86 R, 96–98, 103, 104, 280–299
See application file for complete search history.

(56) References Cited

U.S. PATENT DOCUMENTS

| | | | |
|---|---|---|---|
| 4,906,233 A | 3/1990 | Moriuchi et al. | |
| 5,073,169 A | 12/1991 | Raiken | |
| 5,616,131 A | 4/1997 | Sauer et al. | |
| 5,779,703 A * | 7/1998 | Benoist | 606/54 |
| 5,976,141 A * | 11/1999 | Haag et al. | 606/292 |
| 6,287,281 B1 | 9/2001 | Nishtala et al. | |
| 6,306,146 B1 | 10/2001 | Dinkler | |
| 6,488,664 B1 | 12/2002 | Solomon et al. | |
| 6,723,088 B2 | 4/2004 | Gaskill, III et al. | |
| 7,413,561 B2 | 8/2008 | Raulerson et al. | |
| 8,105,290 B2 | 1/2012 | Wright et al. | |
| 8,182,469 B2 | 5/2012 | Anderson et al. | |
| 8,211,063 B2 | 7/2012 | Bierman et al. | |
| 2006/0089600 A1 | 4/2006 | Bierman et al. | |
| 2007/0158513 A1 | 7/2007 | LeVahn et al. | |
| 2007/0173766 A1 | 7/2007 | Bierman | |
| 2008/0086137 A1* | 4/2008 | Probe | 606/69 |
| 2010/0082028 A1* | 4/2010 | Hajianpour | 606/54 |
| 2012/0310289 A1* | 12/2012 | Bottlang et al. | 606/291 |

* cited by examiner

*Primary Examiner* — Christopher Beccia
(74) *Attorney, Agent, or Firm* — Sorell Lenna & Schmidt LLP

(57) ABSTRACT

A device for holding a surgical tool comprising a base extending along a longitudinal axis between a proximal end and a distal end. The distal end is configured for engagement with a body of a patient to stabilize the device. A retaining portion is disposed at a fixed angle relative to the longitudinal axis and includes an inner surface defining a passageway configured to receive the surgical tool and hold the surgical tool at the fixed angle. A locking element is configured to apply a clamping force to the retaining element such that translation of the surgical tool is prevented in a direction transverse to the longitudinal axis.

23 Claims, 8 Drawing Sheets

SURGICAL TOOL HOLDER

TECHNICAL FIELD

The present disclosure relates to a surgical tool holder configured for use in the treatment of bone defects, such as, for example, bone fractures.

BACKGROUND

Fractures, lesions and collapsing of bone structure can occur in humans due to age, disease or trauma. There are many areas of bone that are prone to collapsing/depression, such as vertebra, the proximal humerus, the tibial plateau, the distal radius and the calcaneus. A surgical tool, such as, for example, an inflatable bone tamp (IBT) may be used to create voids for bone void filler (BVF) material. The IBT or a separate tool is then used to deliver BVF to a bone defect to restore collapsed bone and re-align bone fragments caused by fractures. That is, the bone void filler may be used to fill any voids in the bone, such as, for example, fractures, after the inflatable bone tamp is removed. Precise positioning of the inflatable bone tamp adjacent to the bone defect is essential to properly restore the alignment of the bone. If the inflatable bone tamp is improperly placed, misalignment of the bone can occur. The anatomy of the patient often provides little assistance in maintaining the inflatable bone tamp in a position that places the inflatable bone tamp in a desired position adjacent the bone void, making it difficult to achieve proper placement of the inflatable bone tamp and to hold the tool for delivering BVF. This disclosure provides an improvement over prior art technologies.

SUMMARY

This application is directed to a surgical tool holder for use in treating fractures/lesions in bone. In one embodiment, in accordance with the principles of the present disclosure, a device is provided for holding a surgical tool comprising a base extending along a longitudinal axis between a proximal end and a distal end. The distal end is configured for engagement with a body of a patient to stabilize the device. A retaining portion is disposed at a fixed angle relative to the longitudinal axis and includes an inner surface defining a passageway configured to receive the surgical tool and hold the surgical tool at the fixed angle. A locking element is configured to apply a clamping force to the retaining element such that translation of the surgical tool is prevented in a direction transverse to the longitudinal axis.

In one embodiment, in accordance with the principles of the present disclosure, a device is provided for holding a surgical tool comprising a base extending along a longitudinal axis between a proximal end and a distal end. The distal end is configured for engagement with a body of a patient to stabilize the device. The proximal end includes a retaining element disposed at a fixed relative to the longitudinal axis. The retaining element has an inner surface defining a passageway configured to receive and encase at least a portion of the surgical tool and hold the surgical tool at the fixed angle such that translation of the surgical tool is prevented in a direction parallel to the longitudinal axis.

In one embodiment, in accordance with the principles of the present disclosure, a device is provided for holding a surgical tool comprising a base extending along a longitudinal axis between a proximal end and a distal end. The proximal end is configured for engagement with a body of a patient to stabilize the device. A retaining portion is disposed at the proximal end of the base. The retaining portion defines an opening extending transverse to the longitudinal axis. An insert is configured for disposal in the opening and includes an inner surface defining a passageway configured to receive the surgical tool. The passageway extends at a fixed angle relative to the longitudinal axis such that the surgical tool is disposed at the fixed angle when positioned within the passageway.

BRIEF DESCRIPTION OF THE DRAWINGS

The present disclosure will become more readily apparent from the specific description accompanied by the following drawings, in which.

DETAILED DESCRIPTION

Figure 1:
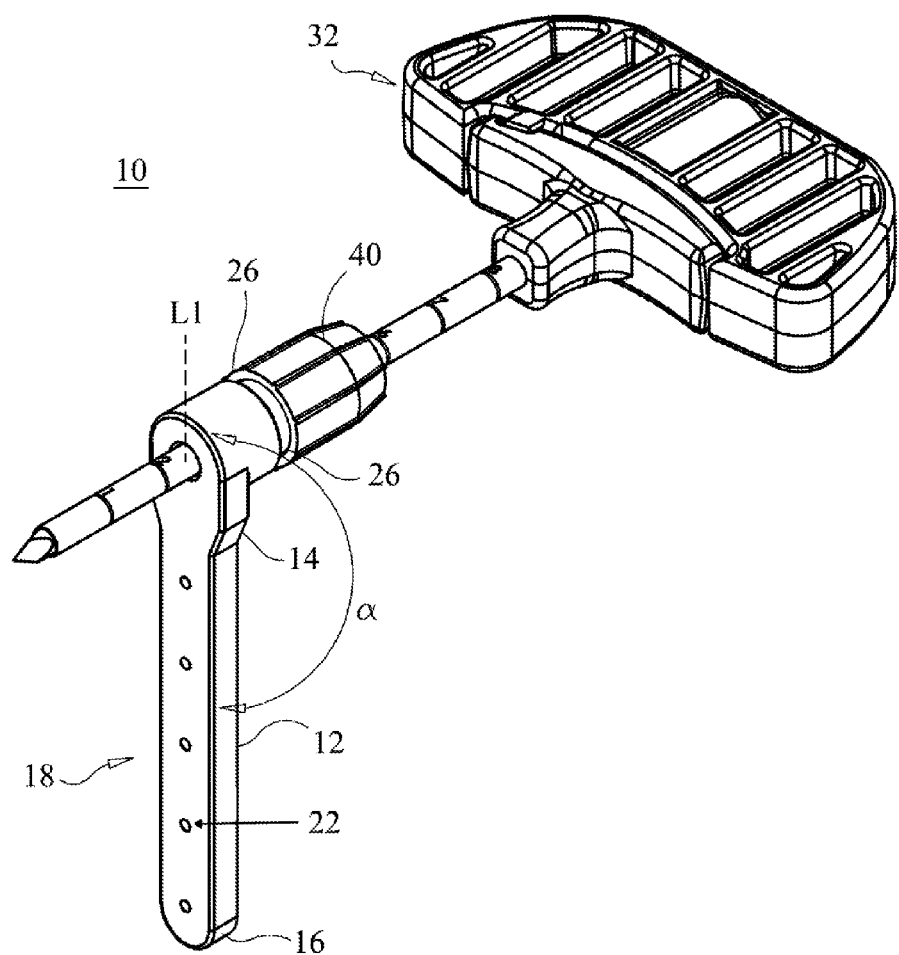
FIG. 1 is a perspective view of one particular embodiment of a surgical tool holding device in accordance with the principles of the present disclosure.

Distal radius factures comprise a substantial portion of traumatic factures. Surgical treatment may involve reduction with metal bone tamps, elevators, fracture fixation with pins, external fixation or plate and screw implants. Inflatable bone tamps (IBT) are also utilized to repair distal radius fractures. An IBT is used percutaneously to reduce comminuted, articular depressions in a controlled manner. The IBT can also be used to reduce non-articular fractures or to create well-defined voids for BVF. Fracture morphologies, such as, for example, "die-punch" fractures are especially suited for correction by an IBT. IBTs are deployed to a surgical site, such as, for example, a bone defect through a working cannula. IBTs create well-defined voids. After the void or void is created by the IBT, the IBT is removed from the cannula and a material, such as, for example, bone void filler is delivered through the cannula and into the void or voids. The bone void filler may be used in conjunction with percutaneous pins, ex-fix, screws, or other implantable hardware for fracture fixation.

Percutaneous delivery of bone filler material through the cannula to bone voids in various parts of a patient's anatomy, such as, for example, a distal radius of the patient can be difficult. For example, if the distal end of the cannula is not open to the bone void of voids when the bone filler material is delivered, the bone void filler material can get stuck in the delivery tool. Furthermore, the distal end of the cannula must be positioned adjacent the bone void or voids to allow the bone void filler to be delivered through the cannula to the bone void or voids. There is often little soft tissue and/or bony anatomy to hold the cannula in a stable position during delivery of the bone filler material. To stabilize the cannula, a surgical assistant is often required to provide an extra pair of hands to hold the cannula while a surgeon delivers the bone filler material to the bone void or voids through the cannula. The present disclosure provides a device that acts as a second pair of hands to hold the cannula at a fixed trajectory to ensure that the cannula is properly positioned relative to the bone void or voids.

In one embodiment, a holding device is provided that includes a two piece collet. The device includes a cannula that slides through the collet. A nut engages the collet to engage the collet with the cannula to prevent the cannula from moving relative to the collet. Prior to engaging the collet with the cannula, the cannula can slide into or out of collet. Sliding of the cannula through the collet becomes more difficult as the collet begins to engage the cannula. When the collet engages the cannula, movement of the cannula relative to the collet is prevented. The cannula trajectory is fixed at a single angle, such as, for example, 90 degrees relative to a longitudinal axis defined by a base of the device. In use, the cannula is positioned within the collet before placing cannula into the anatomy of a patient.

In one embodiment, a single piece snap device is provided. A cannula snaps into a semi-deformable plastic piece having a through hole or passageway. The device is made from a material, such as, for example, polypropylene or polyethylene. The through hole provides a friction fit with the cannula. The cannula can slide into or out of the holder depending on the material and the through hole diameter. The cannula trajectory is fixed at a single angle, such as, for example, 90 degrees to a shaft of the device. In use, the device is placed over the cannula before or after placing cannula into the body.

In one embodiment, a single piece device is provided. The device includes a first portion and a second portion connected by a hinge, such as, for example, a living hinge. A cannula is configured to be positioned in a passageway positioned between the first and second portions. A latch is provided to lock the first and second portions together. The passageway may be lined with a deformable material, such as, for example, silicone rubber, to provide a friction fit with the cannula. The cannula can slide into or out of the passageway depending on material and hole diameter. The cannula trajectory is fixed at a single angle, e.g., 90 degrees relative to a shaft of the device. In use, the device is placed onto the cannula before or after placing cannula into the body.

In one embodiment, a multiple piece snap device is provided. In this embodiment, various angled holders are used to provide a range of angles, such as, for example, 30 degrees, 45 degrees or 90 degrees. In one embodiment, multiple piece silicone inserts are provided with a single outer holder. The holder is configured to receive a silicone insert. Each insert has one fixed trajectory, such as, for example, one insert at 90 degrees to the shaft, another at 60 degrees to shaft. In one embodiment, the holder has a solid silicone insert where the user sticks the cannula through the silicone piece to create the insertion hole. That is, the hole is not preformed.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, distal and proximal, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament and/or bone, repairing a fracture or break in bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of device for holding a surgical tool used for treating bone lesions, fractures and/or collapsed bone and related methods of employing the device in accordance with the principles of the present disclosure. Alternate embodiments are also disclosed. Reference will now be made in detail to the exemplary embodiments of the present disclosure, which are illustrated in the accompanying figures. Turning now to FIGS. 1-11, there are illustrated components of holding devices configured for holding a surgical tool for treating bone lesions, fractures and/or collapsed bone in accordance with the principles of the present disclosure.

The components of the holding device can be fabricated from biologically acceptable materials suitable for medical apparatuses, including metals, synthetic polymers, ceramics, thermoplastic and polymeric material and/or their composites. For example, the components of the holding device, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan, Fe—Mn—Si and Fe—Ni—Co—Ti composites), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers based materials, polymeric rubbers, polyolefin rubbers, semi-rigid and rigid materials, thermoplastic elastomers, thermoset elastomers, elastomeric composites, rigid polymers including polyphenylene, polyamide, polyimide, polyetherimide, polyethylene, epoxy, and composites of metals and calcium-based ceramics, composites of PEEK and calcium based ceramics, and combinations of the above materials.

Various components of the holding device may have material composites, including the above materials, to achieve various desired characteristics such as strength, rigidity, elasticity, compliance, and biomechanical performance, durability and to provide a non-stick surface. The components of the holding device may be monolithically formed, extruded, coextruded, hot molded, cold molded, press molded, integrally connected or include fastening elements and/or coupling components, as described herein.

Figure 2:
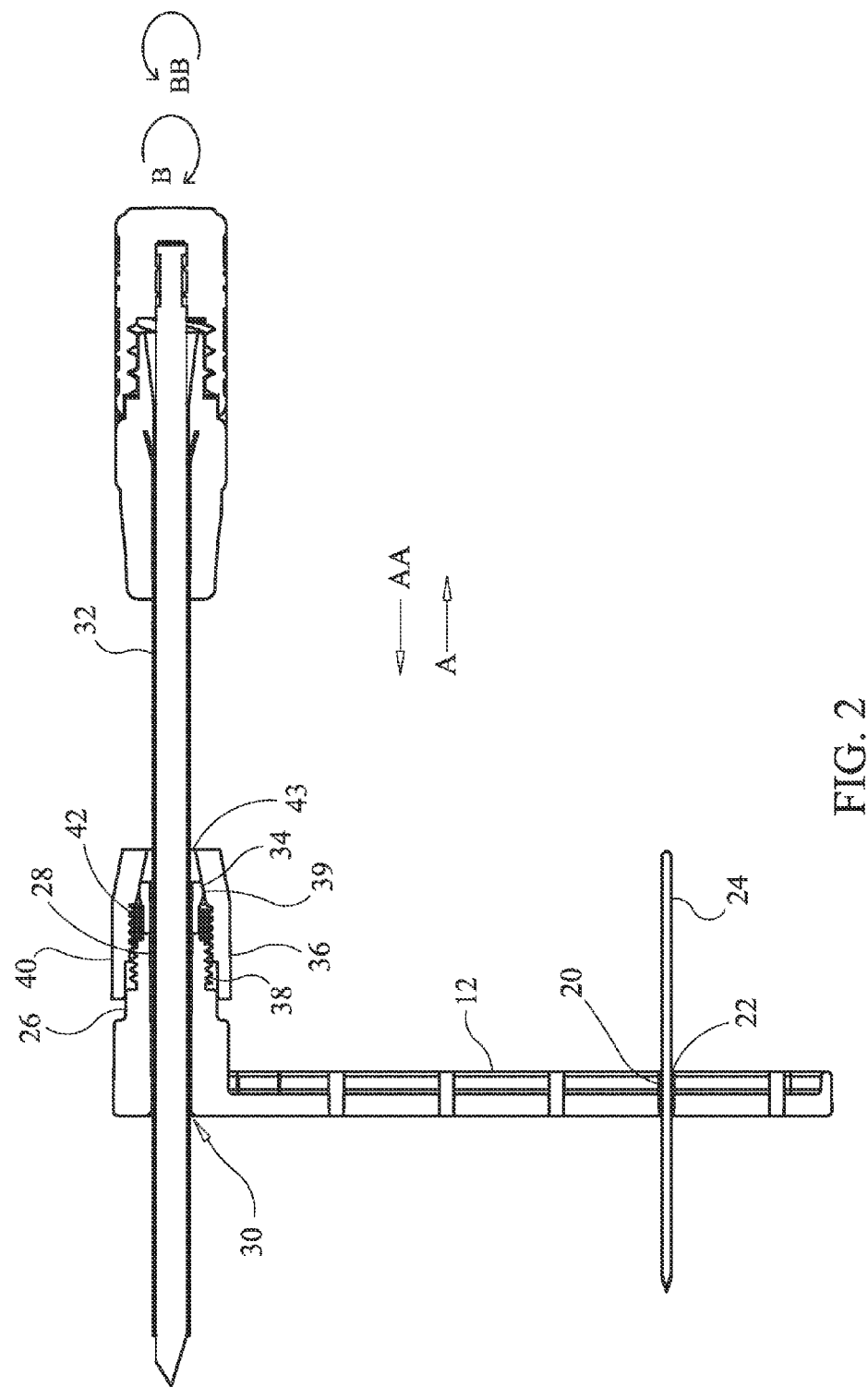
FIG. 2 is a side, cross sectional view of the device shown in FIG. 1.

In one embodiment, shown in FIGS. 1-2, a surgical tool holding device 10 is provided in accordance with the present disclosure. Device 10 includes a base 12 extending along a longitudinal axis L1 between a proximal end 14 and a distal end 16. Distal end 16 includes an engagement portion 18 configured for attaching device 10 to a body of a patient. In some embodiments, base 12 can include a surface that may be smooth, rough, textured, porous, semi-porous, dimpled and/or polished such that it facilitates engagement with the body. In some embodiments, the cross-section geometry of base 12 may have various configurations, such as, for example, round, oval, oblong, triangular, polygonal having planar or arcuate side portions, irregular, uniform or non-uniform.

Portion 18 includes an inner surface 20 that defines at least one aperture, such as, for example, opening 22. Opening 22 is configured to receive an engagement device, such as, for example a pin 24. It is envisioned that portion 18 may include one or a plurality of openings 22. It is further envisioned that device 10 may include one or a plurality of pins, corresponding to the number of openings 22. It is contemplated that pins 24 may comprise a wire, such as, for example, a K-wire. As shown in FIG. 2, openings 22 are arranged perpendicular to axis L1. It is envisioned that openings 22 may be disposed through angular ranges in various orientations relative to axis L1, such as, for example, transverse and/or other angular orientations such as acute or obtuse, and/or may be offset or staggered. In some embodiments, inner surface 20 may be rough, textured, porous, semi-porous, dimpled and/or polished to facilitate engagement with pin 24. In some embodiments, other engagement devices may be used, such as, for example, a nail configuration, barbs, expanding elements, raised elements and/or spikes to facilitate engagement of base 12 with the body of the patient. In one embodiment, base 12 includes an adhesive surface or clamping mechanism configured for noninvasive engagement with the body of the patient.

End 14 includes a retaining portion 26 disposed at a fixed angular orientation α relative to axis L1. Angle α ranges from 0-180 degrees with respect to axis L1 such that portion 26 provides a fixed trajectory into the body. It is envisioned that angle α may also range from 1-179 degrees with respect to axis L1. A first end of portion 26 includes a collet 34. Portion 26 includes an inner surface 28 that defines a passageway 30 extending transverse to longitudinal axis L1. Passageway 30 is configured to receive a surgical tool, such as, for example, a cannula 32. In some embodiments, inner surface 28 may be rough, textured, porous, semi-porous, dimpled and/or polished to facilitate engagement with cannula 32. As shown in FIG. 2, collet 34 is round in cross section, however, collet 34 may have various configurations, such as, for example, oval, oblong, triangular, polygonal having planar or arcuate side portions, irregular, uniform or non-uniform. Collet 34 includes an outer surface 36 that includes a threaded portion 38 and a portion 39 that is free of threads.

Device 10 includes a locking element, such as, for example, a nut 40. Nut 40 includes a first end having a threaded inner surface 42 and a second end having with an angled inner surface 43 that is free of threads. That is, surface 42 is tapered from a section of surface 43 adjacent surface 42 to a section of surface 43 opposite the section of surface 43 adjacent surface 42. Threaded inner surface 42 is configured to engage portion 38. As threaded inner surface 42 engages portion 38, nut 40 is rotated in the direction shown by arrow B or arrow BB such that nut 40 translates relative to base 12 in the direction shown by arrow A. As nut 40 translates in the direction shown by arrow A, angled inner surface 43 engages portion 39 causing inner surface 28 to engage cannula 32. Because surface 43 is angled, rotation of nut 40 in the direction shown by arrow B or arrow BB allows for incremental tightening of surface 28 about cannula 32 such that a restrictive force applied to cannula 32 can be adjusted by altering the amount of rotation of nut 40. When portion 38 is fully threaded with surface 42, cannula 32 becomes fixed relative to collet 34 so as to fix cannula 32 at a fixed angle relative to axis L1. That is, engaging inner surface 28 with cannula 32 prevents cannula 32 from moving in the direction shown by arrow A or the direction shown by arrow AA.

In operation, assembly and use, device 10 is employed with a surgical procedure for treatment of a bone disorder, such as, for example, a fracture in a vertebra or extremity of a patient. Device 10 is inserted into or on the anatomy of the patient. Pins 24 are positioned within through openings 22 and are disposed in the anatomy of the patient, such as, for example, tissue, to fix or stabilize device 10 relative to the anatomy of the patient. Once device 10 is stabilized, cannula 32 is positioned within passageway 30 such that a distal end of cannula 32 is positioned adjacent the bone disorder and cannula 32 is movable in the direction shown by arrow A or the direction shown by arrow AA within passageway 30. The position of cannula 32 relative to the bone disorder can therefore be altered by sliding cannula 32 in the direction shown by arrow A or the direction shown by arrow AA.

Surface 42 is positioned so as to engage portion 38. Nut 40 is then rotated in the direction shown by arrow B or arrow BB such that nut 40 translates relative to base 12 in the direction shown by arrow A until surface 43 engages portion 39. Nut 40 is rotated in the direction shown by arrow B or arrow BB until surface 28 engages cannula 32 in a manner that prevents cannula 32 from moving in the direction shown by arrow A or the direction shown by arrow AA.

An inflatable bone tamp may be delivered through cannula 32 to a location adjacent the bone disorder or defect. The inflatable bone tamp may then be expanded to create a cavity or void in the bone. After the cavity or void is formed in the bone, the inflatable bone tamp is removed from device 10.

Bone filler material is then delivered through cannula 32 or with a separate bone filler delivery device and into the cavity or void so as to at least partially fill the cavity or void and realign fragments of the fracture. Device 10 maintains cannula 32 in a stabilized orientation with respect to the body such that a single practitioner can administer the bone filling material in a steady manner.

Figure 3:
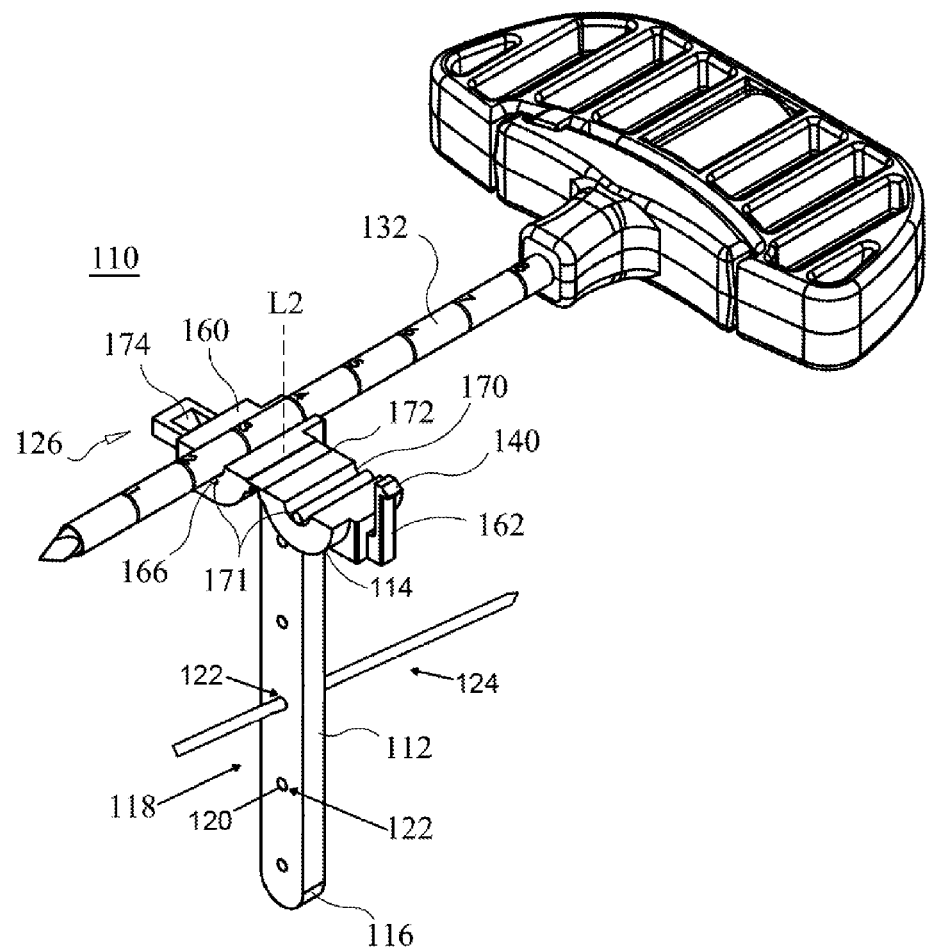
FIG. 3 is a perspective view of one particular embodiment of a surgical tool holding device in accordance with the principles of the present disclosure.
Figure 4:
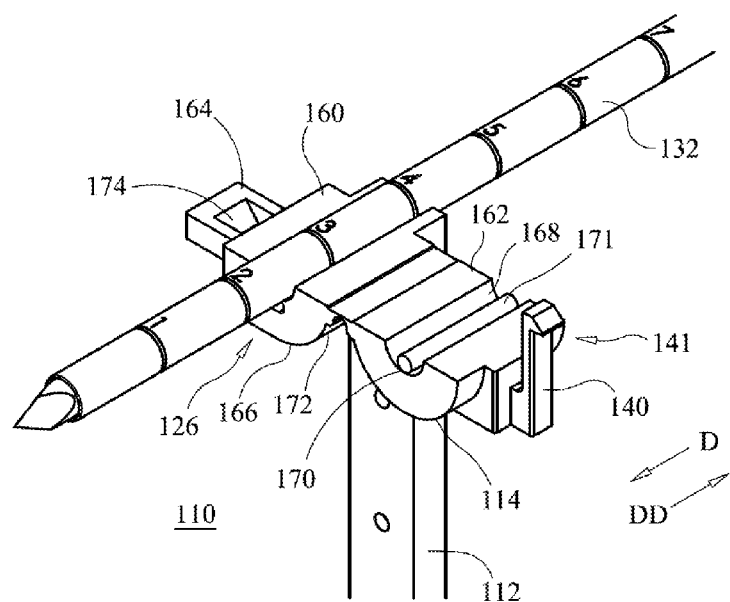
FIG. 4 is a perspective view of components of the device shown in FIG. 3.
Figure 5:
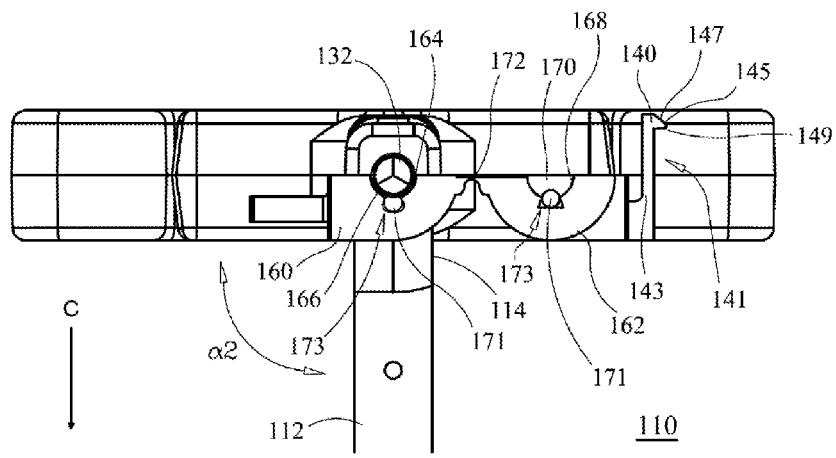
FIG. 5 is a front view of components of the device shown in FIG. 3.
Figure 6:
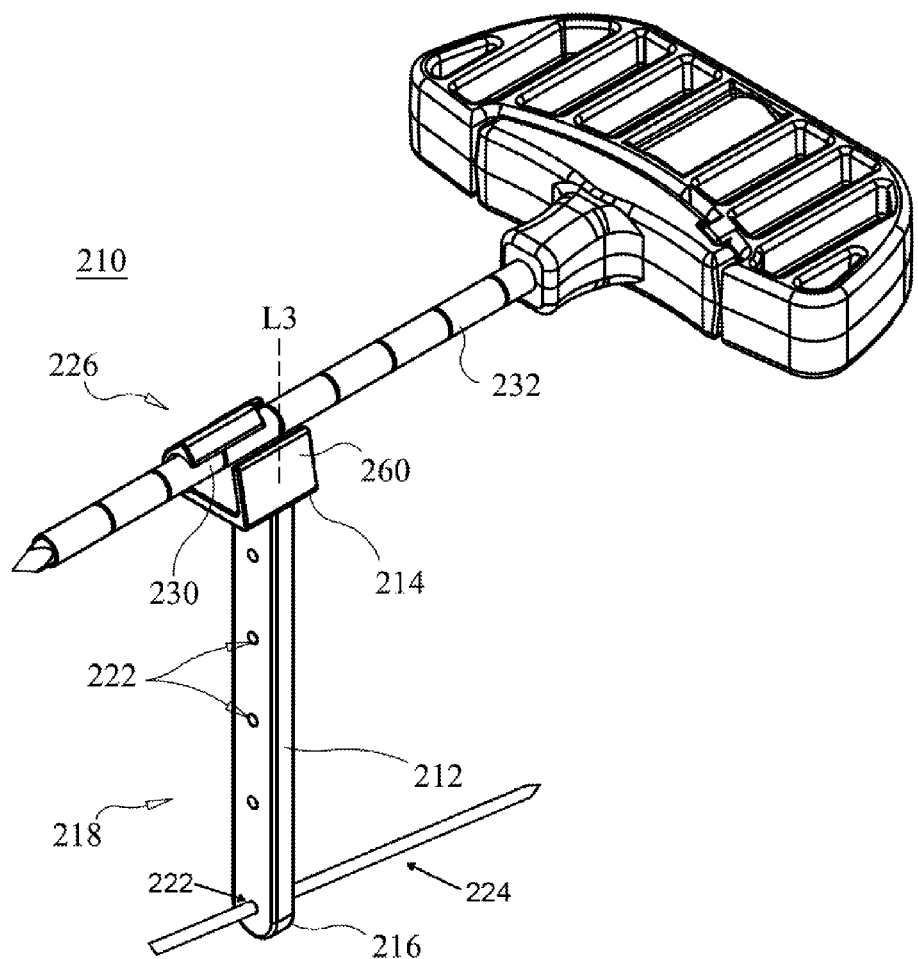
FIG. 6 is a perspective view of one particular embodiment of a surgical tool holding device in accordance with the principles of the present disclosure.
Figure 7:
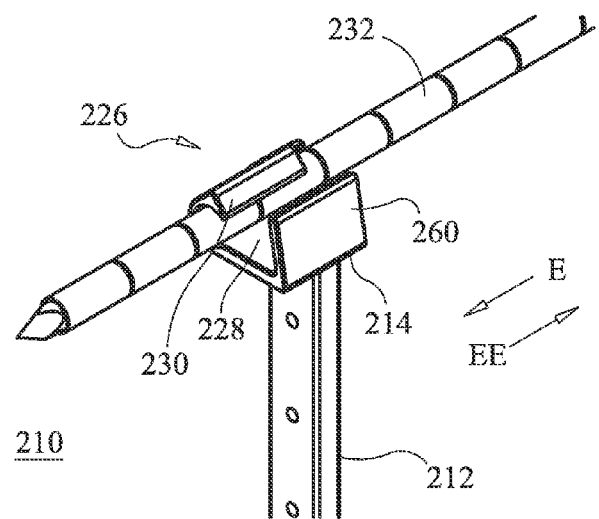
FIG. 7 is a perspective view of components of the device shown in FIG. 6.
Figure 8:
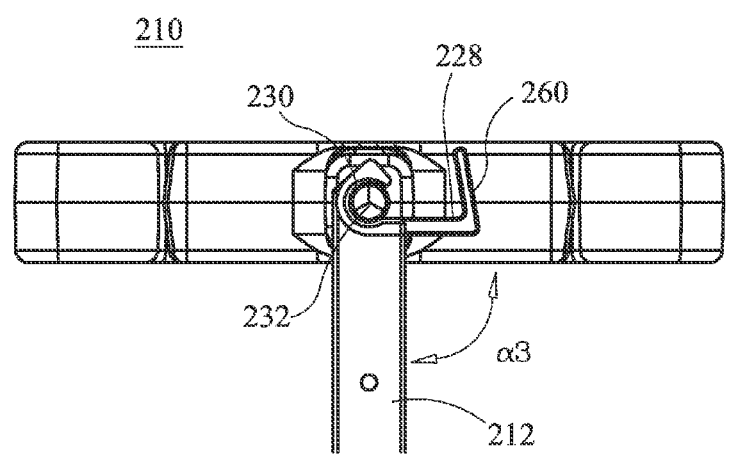
FIG. 8 is a front view of components of the device shown in FIG. 6.
Figure 9C:
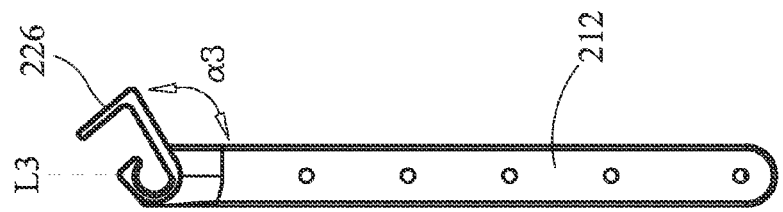
FIGS. 9a-9c are various angular variations of the device shown in FIG. 6.
Figure 9B:
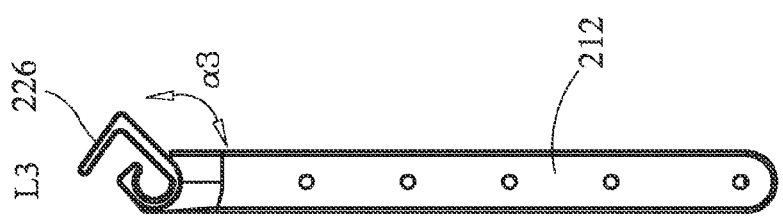
Figure 9A:
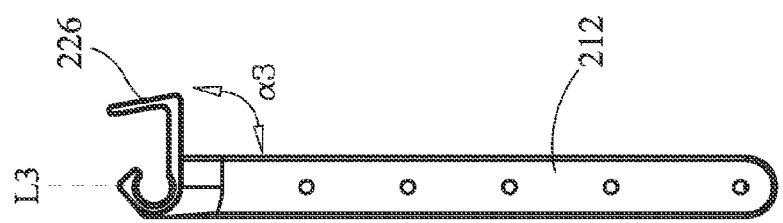

In one embodiment, shown in FIGS. 3-5, a device 110, in accordance with the principles of the present disclosure, includes a base 112, similar to base 12, described above. Base 112 extends along a longitudinal axis L2 between a proximal end 114 and a distal end 116. Distal end 116 includes an engagement portion 118 configured for attaching device 110 to a body of a patient. Base 112 includes an inner surface 120 that defines at least one aperture, such as, for example, opening 122. Opening 122 is configured to receive an engagement device, such as, for example a pin or K-wire 124.

Device 110 includes a retaining portion 126 positioned at end 114 at a fixed angular orientation α2 relative to longitudinal axis L2. Angle α2 ranges from 0-180 degrees with respect to axis L2 such that it provides a fixed trajectory into the body. It is envisioned that angle α2 may also range from 1-179 degrees with respect to axis L2. Portion 126 includes a first portion 160 and a second portion 162.

First portion 160 includes an inner surface 164 that defines a semi-cylindrical passageway 166. Passageway 166 is configured to receive a portion of a cylindrical surgical tool, such as, for example, a cannula 132. In some embodiments, inner surface 164 may be rough, textured, porous, semi-porous, dimpled and/or polished to facilitate engagement with cannula 132. Second portion 162 includes an inner surface 168 that defines a semi-cylindrical passageway 170. Passageway 170 is configured to receive a portion of cannula 132. In some embodiments, inner surface 168 may be rough, textured, porous, semi-porous, dimpled and/or polished to facilitate engagement with cannula 132. Passageways 166, 170 each have a uniform width along a length thereof. It is envisioned that all or only a portion of passageway 166 and/or passageway 170 may have alternate cross section configurations, such as, for example, oval, oblong, triangular, square, polygonal, irregular, uniform, non-uniform, offset, staggered, undulating, arcuate, variable and/or tapered. In some embodiments, one of passageways 166, 170 is configured such that cannula may be snap fit into either passageway 166 or passageway 170.

In some embodiments, at least one of passageways 166, 170 have a material 171 disposed therein to enhance engagement between passageway 166 and/or passageway 170 with cannula 132. It is envisioned that material 171 may be an elastic material or a deformable material, such as, for example, silicone or elastomer (e.g., synthetically produced butyl rubber or neoprene or a natural rubber). In some embodiments, passageways 166, 170 each include a polygonal trough 173 extending into a bottommost portion of passageways 166, 170 so as to be in communication with passageways 166, 170. In some embodiments, material 171 is in the form of a cylinder having a maximum width that is greater than a minimum width of trough 173 so as to maintain material 171 in trough 173. As shown in FIG. 5, material 171 has a maximum height that is greater than a maximum height of troughs 173 such that at least a portion of material 171 extends into passageway 166 or passageway 170 so as to engage cannula 132. It is contemplated that all or only a portion of troughs 173 and/or material 171 may be variously configured and dimensioned, such as, for example, circular, oval, oblong, triangular, square, rectangular, polygonal, irregular, uniform, non-uniform, offset, staggered, tapered, consistent or variable, depending on the requirements of a particular application.

First portion 160 and second portion 162 are connected via a hinge 172, such as, for example, a living hinge. Hinge 172 allows second portion 162 to rotate about first portion 160 and close around cannula 132 such that passageways 166 and 170 form a single passageway to encase cannula 132. In some embodiments, hinge 172 may include a barrel hinge, pivot hinge, butt/mortise hinge, case hinge, continuous hinge or piano hinge, concealed hinge, butterfly hinge or Parliament (UK) hinge, flag hinge, strap hinge, H hinge, HL hinge, counterflap hinge, flush hinge, coach hinge, rising butt hinge, double action spring hinge, tee hinge, friction hinge, security hinge, cranked hinge or stormproof hinge, lift-off hinge or self-closing hinge. In some embodiments, portions 160, 162 and hinge 172 are made from the same material, the material having a reduced thickness at hinge 172 to facilitate bending. In some embodiments, portions 160, 162 are made from the same material and hinge 172 comprises a material that is different from a material that portions 160, 162 are made from. In some embodiments, hinge 172 comprises a plurality of hinges that are each spaced apart from one another.

Device 110 includes a locking element, such as, for example, a latch 140. Latch 140 is disposed with second portion 162 and is configured to engage with first portion 160 via a rectangular opening 174 extending parallel to axis L2. Engagement of latch 140 with opening 174 causes first portion 160 and second portion 162 to create a clamping force around cannula 132 such that movement of cannula 132 is restricted. It is envisioned that opening 174 may be disposed at alternate orientations relative to longitudinal axis L2, such as, for example, transverse, perpendicular and/or other angular orientations such as acute or obtuse and/or may be offset or staggered and/or may be disposed at alternative angular orientations relative to axis L2, depending on the requirements of a particular application. It is further envisioned that all or only a portion of opening 174 may be variously configured and dimensioned, such as, for example, circular, oval, oblong, triangular, square, rectangular, polygonal, irregular, uniform, non-uniform, offset, staggered, tapered, consistent or variable, depending on the requirements of a particular application.

In some embodiments, latch 140 includes a resilient tab 141 extending proximally from portion 162 in a direction that is parallel to axis L2. Tab 141 includes a distal portion or arm 143 having a uniform width or diameter and a proximal portion including a catch 145 having a width or diameter that is greater than that of portion 143. Catch 145 extends in a direction that is perpendicular to axis L2. Catch 145 includes a tapered upper surface 147 and a planar lower surface 149. Surface 147 extends at an acute angle relative to axis L2 and surface 149 extends perpendicular to axis L2. To engage latch 140 with opening 174, latch 140 is positioned adjacent opening 174 such that surface 147 engages surface 164. Tab 141 is then translated in a direction shown by arrow C such that catch 145 moves through opening 164 and surface 149 engages a distal surface of portion 160 extending transverse to axis L2. In some embodiments, tab 141 is resiliently biased such that portion 143 engages surface 164 when surface 149 engages the distal surface of portion 160. It is envisioned that surface 147 and/or surface 149 may be disposed at alternate orientations relative to longitudinal axis L2, such as, for example, transverse, perpendicular and/or other angular orientations such as acute or obtuse and/or may be offset or staggered and/or may be disposed at alternative angular orientations relative to axis L2, depending on the requirements of a particular application.

In operation, assembly and use, device 110 is employed with a surgical procedure for treatment of a bone disorder, such as, for example, a fracture in a vertebra or extremity of a patient. Device 110 is inserted into or on the anatomy of the patient. Pins 124 are positioned within through openings 122 and are disposed in the anatomy of the patient, such as, for example, tissue, to fix or stabilize device 110 relative to the anatomy of the patient. Once device 110 is stabilized, cannula 132 is positioned within passageway 166 such that a distal end of cannula 132 is positioned adjacent the bone disorder or defect and cannula 132 is movable within passageway 166 in the direction shown by arrow D or the direction shown by arrow DD. The position of cannula 132 relative to the bone disorder can therefore be altered by sliding cannula 132 in the direction shown by arrow D or the direction shown by arrow DD.

Latch 140 is positioned adjacent opening 174 such that surface 147 engages surface 164. Tab 141 is then translated in a direction shown by arrow C such that catch 145 moves through opening 164 and surface 149 engages a distal surface of portion 160 extending transverse to axis L2. Positioning latch 140 in opening 174 fixes cannula relative to device 110 such that cannula is prevented from moving in the direction shown by arrow D or the direction shown by arrow DD within passageways 166, 170.

An inflatable bone tamp may be delivered through cannula 132 to a location adjacent the bone disorder or defect. The inflatable bone tamp may then be expanded to create a cavity or void in the bone. After the cavity or void is formed in the bone, the inflatable bone tamp is removed from device 110. Bone filler material is then delivered through cannula 132 and into the cavity or void so as to at least partially fill the cavity or void and realign fragments of the fracture and/or elevate collapsed bone to its proper height. Device 110 maintains cannula 132 in a stabilized orientation with respect to the body such that a single practitioner can administer the bone filling material in a steady manner.

In one embodiment, shown in FIGS. 6-9c, a surgical tool holding device 210, in accordance with the present disclosure, is provided that includes a base 212. Base 212 extends along a longitudinal axis L3 between a proximal end 214 and a distal end 216. Distal end 216 includes an engagement portion 218 configured for attaching device 210 to a body of a patient.

Device 210 includes a retaining element 226. Retaining element 226 is disposed with end 214 at a fixed angular orientation α3. As shown in in FIGS. 9a-9c, angle α3 ranges from 0-180 degrees with respect to axis L3. Element 226 includes an inner surface 228 that defines a passageway 230. Passageway 230 is configured to receive and encase a portion of a cannula 232 such that cannula 232 is held at a fixed angle relative to axis L3. It is envisioned that angle α3 may range from 1-179 degrees relative to axis L3.

In some embodiments, retaining element 226 includes a semi-deformable material, such as, for example, polypropylene such that a portion of passageway 230 snap fits around cannula 232. This tight fit between passageway 230 and cannula 232 provides for a friction fit between passageway 230 and cannula 232. Element 226 includes a flange, such as, for example, a wall 260 configured to prevent cannula 232 from disengaging from passageway 230. Wall 260 extends at an acute angle relative to axis L3. It is envisioned that passageway 230 and/or wall 260 may be disposed at alternate orientations relative to longitudinal axis L3, such as, for example, transverse, perpendicular and/or other angular orientations such as acute or obtuse and/or may be offset or staggered and/or may be disposed at alternative angular orientations relative to axis L3, depending on the requirements of a particular application.

In operation, assembly and use, device 210 is employed with a surgical procedure for treatment of a bone disorder, such as, for example, a fracture in a vertebra or extremity of a patient. Device 210 is inserted into or onto the anatomy of the patient. Pins 224 are positioned within through openings 222 extending perpendicular to axis L3 through base 212 and are disposed in the anatomy of the patient, such as, for example, tissue, to fix or stabilize device 210 relative to the anatomy of the patient. Once device 210 is stabilized, cannula 232 is positioned within passageway 230 such that a distal end of cannula 232 is positioned adjacent the bone disorder or defect and cannula 232 is movable within passageway 230 in the direction shown by arrow E or the direction shown by arrow EE. The position of cannula 232 relative to the bone disorder can therefore be altered by sliding cannula 232 in the direction shown by arrow E or the direction shown by arrow EE.

An inflatable bone tamp may be delivered through cannula 232 to a location adjacent the bone disorder or defect. The inflatable bone tamp may then be expanded to create a cavity or void in the bone. After the cavity or void is formed in the bone, the inflatable bone tamp is removed from device 210. Bone filler material is then delivered through cannula 232 and into the cavity or void so as to at least partially fill the cavity or void and realign fragments of the fracture and/or elevate collapsed bone to its proper height. Device 210 maintains cannula 232 in a stabilized orientation with respect to the body such that a single practitioner can administer the bone filling material in a steady manner.

Figure 10:
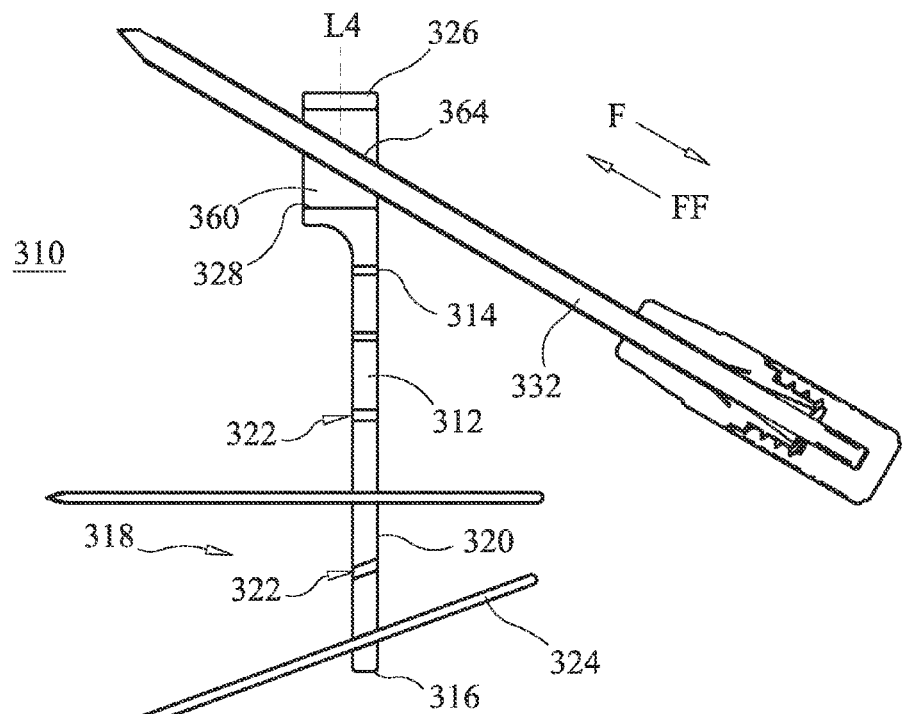
FIG. 10 is side cross sectional view of one particular embodiment of a surgical tool holding device in accordance with the principles of the present disclosure.
Figure 11:
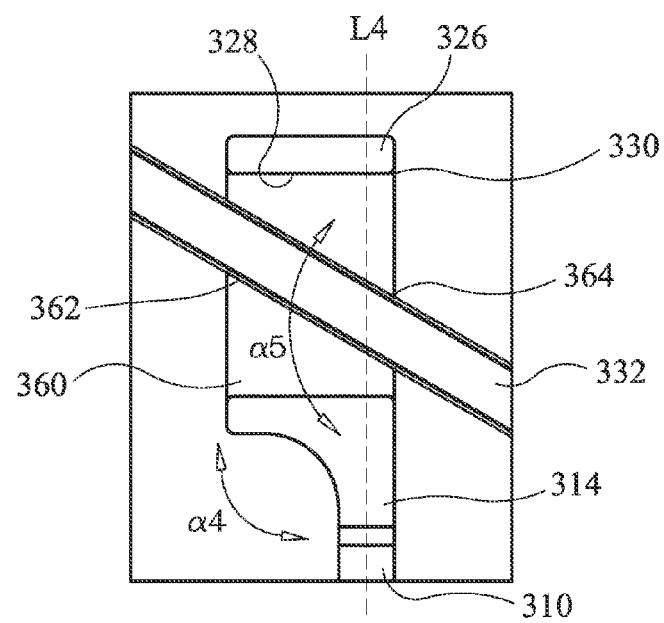
FIG. 11 is a side cross sectional view of components of the device shown in FIG. 10.

In one embodiment, shown in FIGS. 10 and 11, a surgical tool holding device 310, in accordance with the present disclosure, is provided that includes a base 312. Base 312 extends along a longitudinal axis L4 between a proximal end 314 and a distal end 316. Distal end 316 includes an engagement portion 318 configured for attaching device 310 to a body of a patient.

Base 312 includes an inner surface 320 that defines at least one aperture, such as, for example, opening 322. Opening 322 is configured to receive an engagement device, such as, for example a pin or K-wire 324. It is envisioned that device 310 may include one or a plurality of openings 322. In some embodiments, device 310 includes a plurality of openings 322 extending perpendicular to axis L4 and a plurality of openings 322 extending at an acute angle relative to axis L4. As shown in FIG. 10, the openings 322 that extend at an acute angle relative to axis L4 are positioned distally of the openings 322 that extend perpendicular to axis L4. However, it is envisioned that this configuration may be reversed. That is, the openings 322 that extend at an acute angle relative to axis L4 may be positioned proximally of the openings 322 that extend perpendicular to axis L4. It is further envisioned that the openings 322 that extend at an acute angle relative to axis L4 may alternate with the openings 322 that extend perpendicular to axis L4 along the length of base 312.

Device 310 includes a retaining element 326 extending through end 314 including an inner surface 328 that defines a passageway 330 configured to receive an insert 360. As shown in FIGS. 10 and 11, passageway 330 extends perpendicular to axis L4 and has a polygonal cross-sectional configuration. It is envisioned that passageway 330 may be disposed at alternate orientations relative to longitudinal axis L3, such as, for example, transverse, perpendicular and/or other angular orientations such as acute or obtuse and/or may be offset or staggered and/or may be disposed at alternative angular orientations relative to axis L4 depending on the requirements of a particular application. In some embodiments, passageway is variously configured and dimensioned, such as, for example, circular, oval, oblong, triangular, square, rectangular, polygonal, irregular, uniform, non-uniform, offset, staggered, tapered, consistent or variable, depending on the requirements of a particular application.

Insert 360 is configured for disposal with passageway 330. Insert 360 is made from a material, such as, for example, silicone. Insert 360 is resiliently biased configuration such that insert 360 is deformable to a second orientation and expands back to a first orientation. In some embodiments, all or only a portion of insert 360 may have a semi-rigid, rigid or elastic configuration, and/or have elastic properties, such as the elastic properties corresponding to the material examples described above, such that insert 360 provides a selective amount of expansion, contraction, collapse and/or extension. In some embodiments, insert 360 may be compressible in an axial direction. That is, insert 360 may be maintained within passageway 330 by a snap-fit or friction-fit configuration. Insert 360 can include a plurality of separately attachable or connectable portions or sections, such as bands or loops, or may be monolithically formed as a single continuous element. In one embodiment, insert 360 is integrally formed with end 314 such that insert 360 and base 312 are a single piece. That is, base 312 and insert 360 are monolithic.

Insert 360 includes an inner surface 362 that defines a passageway 364. Passageway 364 is configured to receive a cannula 332. Passageway 364 defines a second fixed angular orientation α5. Angle α5 ranges from 0-180 degrees with respect to axis L4 or from 1-179 degrees relative to axis L4. Provision of two angular orientations allows angulation in two planes. It is envisioned that device 310 may be part of a kit that includes multiple inserts 360 each having a passageway 364 extending at a different angle relative to axis L4 in order to provide a medical practitioner with a variety of options regarding the angle relative to axis L4 at which cannula 332 is to be held by device 310.

In operation, assembly and use, device 310 is employed with a surgical procedure for treatment of a bone disorder, such as, for example, a fracture in a vertebra or extremity of a patient. Pins 324 are positioned within through openings 322 and are disposed in the anatomy of the patient, such as, for example, tissue, to fix or stabilize device 310 relative to the anatomy of the patient. Once device 310 is stabilized, insert 360 is positioned within passageway 330. Cannula 332 is then positioned within passageway 364 such that a distal end of cannula 332 is positioned adjacent the bone disorder and cannula 332 is movable in the direction shown by arrow F or the direction shown by arrow FF within passageway 364. The position of cannula 332 relative to the bone disorder can therefore be altered by sliding cannula 332 in the direction shown by arrow F or the direction shown by arrow FF.

An inflatable bone tamp may be delivered through cannula 332 to a location adjacent the bone disorder or defect. The inflatable bone tamp may then be expanded to create a cavity or void in the bone. After the cavity or void is formed in the bone, the inflatable bone tamp is removed from device 310. Bone filler material is then delivered through cannula 332 and into the cavity or void so as to at least partially fill the cavity or void and realign fragments of the fracture and/or elevate collapsed bone to its proper height. Device 310 maintains cannula 332 in a stabilized orientation with respect to the body such that a single practitioner can administer the bone filling material in a steady manner.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A device for holding at least one surgical tool comprising:
    a base extending along a longitudinal axis between a proximal end and a distal end, the distal end being configured for engagement with a body of a patient to stabilize the device;
    a retaining portion disposed at the proximal end of the base, the retaining portion defining a first passageway extending transverse to the longitudinal axis; and
    an insert configured for disposal in the first passageway, and including an inner surface defining a second passageway configured to receive at least a portion of the at least one surgical tool, the second passageway extending at one of at least two fixed angles relative to the longitudinal axis such that the at least a portion of the at least one surgical tool is disposed at the one of at least two fixed angles when the at least a portion of the at least one surgical tool is disposed in the second passageway;
    wherein the at least two fixed angles, define angulation in at least two planes for the at least one surgical tool; and
    wherein the insert is removable and the first passageway is configured to receive a plurality of the inserts, each of the inserts in the plurality of the inserts defining one of a plurality of passageways, each passageway in the plurality of passageways being disposed at one of a plurality of different fixed angles relative to the longitudinal axis in the at least two planes for the at least one surgical tool.

2. A device as recited in claim 1, wherein one of the at least two fixed angles is in a range from 0 degrees to 180 degrees in one of the at least two planes for the at least one surgical tool.

3. A device as recited in claim 1, wherein the base includes at least one aperture configured to receive an engagement device for attachment to the body.

4. A kit for holding at least one surgical tool during surgery on a body of a patient, the kit comprising:
    a surgical tool holding device comprising:
        a base extending along a longitudinal axis between a proximal end and a distal end, the distal end being configured for engagement with a body of a patient, and
        a retaining element configured for disposal at the proximal end of the base, the retaining element defining a first passageway extending transverse to the longitudinal axis;
    a plurality of inserts, each insert of the plurality of inserts being configured for disposal in the first passageway, and including an inner surface defining a second passageway, each second passageway configured to receive at least a portion of the at least one surgical tool, and each second passageway extending at one of at least two fixed angles relative to the longitudinal axis such that the at least a portion of the at least one surgical tool is disposed at the one of at least two fixed angles when the at least a portion of the at least one surgical tool is disposed in the second passageway;
    wherein the at least two fixed angles define angulation in at least two planes for the at least a portion of the at least one surgical tool; and
    wherein the insert is removable and the first passageway is configured to receive a plurality of the inserts, each of the inserts in the plurality of the inserts defining one of a plurality of passageways, each passageway in the plurality of passageways being disposed at one of a plurality of different fixed angles relative to the longitudinal axis in the at least two planes for the at least one surgical tool.

5. A kit as recited in claim 4, wherein the base comprises a plurality of openings and the kit further comprises at least one pin configured for disposal in one of the openings.

6. A kit as recited in claim 5, wherein the at least one pin comprises a plurality of pins.

7. A kit as recited in claim 5, wherein the at least one pin is a K-wire.

8. A kit as recited in claim 5, wherein at least one of the plurality of openings extends substantially perpendicular to the longitudinal axis and at least one of the plurality of openings extends at an acute angle relative to the longitudinal axis.

9. A kit as recited in claim 4, wherein the at least one surgical tool is a cannula, and the kit further comprises the cannula.

10. A kit comprising:
a device comprising:
a base extending along a longitudinal axis and comprising a proximal end, and
a retaining element positioned at the proximal end of the base, the retaining portion defining an opening; and
at least one insert configured for disposal in the opening, and including an inner surface defining a passageway, the passageway configured to receive at least a portion of at least one surgical tool, the passageway extending at one of at least two fixed angles relative to the longitudinal axis when the at least the portion of the at least one surgical tool is disposed in the passageway;
wherein the at least two fixed angles define angulation in at least two planes for the at least a portion of the at least one surgical tool; and
wherein the insert is removable and the first passageway is configured to receive a plurality of the inserts, each of the inserts in the plurality of the inserts defining one of a plurality of passageways, each passageway in the plurality of passageways being disposed at one of a plurality of different fixed angles relative to the longitudinal axis in the at least two planes for the at least one surgical tool.

11. A kit as recited in claim 10, wherein the base comprises a plurality of openings and the kit further comprises at least one pin configured for disposal in one of the openings.

12. A kit as recited in claim 11, wherein the at least one pin comprises a plurality of pins.

13. A kit as recited in claim 11, wherein the at least one pin is a K-wire.

14. A kit as recited in claim 11, wherein at least one of the plurality of openings extends perpendicular to the longitudinal axis and at least one of the plurality of openings extends at an acute angle relative to the longitudinal axis.

15. A kit as recited in claim 10, wherein the surgical tool is a cannula, and the kit further comprises the cannula.

16. A kit as recited in claim 10, wherein the insert comprises silicone.

17. A device as recited in claim 1, wherein the first passageway extends one of perpendicular to the longitudinal axis, at an acute angle with respect to the longitudinal axis, and at an obtuse angle with respect to the longitudinal axis.

18. A device as recited in claim 1, wherein the insert comprises one of a deformable material, an elastic material, a semi-rigid material, and a rigid material.

19. A device as recited in claim 1, wherein the insert is maintained in the first passageway by one of a snap fit and a friction fit.

20. A device as recited in claim 1, wherein the insert includes at least one separately attachable portion, the at least one separately attachable portion being one of a band, a loop, and a monolithically-formed single continuous element.

21. A device as recited in claim 1, wherein one of the at least two angular orientations in the one of the at least two planes is in a range from 1° to 179°.

22. A device as recited in claim 1, wherein the insert is configured to be immobile in the retaining portion.

23. A device as recited in claim 1, wherein the insert is configured to allow the at least one surgical tool to be movable within the second passageway in at least one of a plurality of directions.

* * * * *

UNITED STATES PATENT AND TRADEMARK OFFICE
CERTIFICATE OF CORRECTION

PATENT NO. : 9,149,317 B2
APPLICATION NO. : 13/790825
DATED : October 6, 2015
INVENTOR(S) : Arthur et al.

It is certified that error appears in the above-identified patent and that said Letters Patent is hereby corrected as shown below:

On The Title Page

In Item (71), under "Applicant", in Column 1, Line 1, delete "SARL, Neuchatel" and insert -- SÀRL, Neuchâtel --, therefor.

In Item (73), under "Assignee", in Column 1, Line 1, delete "SARL, Neuchatel" and insert -- SÀRL, Neuchâtel --, therefor.

In Item (74), under "Attorney, Agent, or Firm", in Column 2, Line 1, delete "Sorell Lenna & Schmidt" and insert -- Sorell, Lenna & Schmidt, --, therefor.

In The Specification

In Column 2, Line 18, delete "side," and insert -- side --, therefor.

In Column 8, Line 59, delete "opening 164" and insert -- opening 174 --, therefor.

In Column 9, Line 23, delete "opening 164" and insert -- opening 174 --, therefor.

In Column 9, Line 50, delete "shown in in" and insert -- shown in --, therefor.

Signed and Sealed this
Fifteenth Day of March, 2016

Michelle K. Lee
*Director of the United States Patent and Trademark Office*